US008420494B1

(12) United States Patent
Holm-Kennedy

(10) Patent No.: US 8,420,494 B1
(45) Date of Patent: Apr. 16, 2013

(54) DISTRIBUTED CHANNEL BIPOLAR DEVICES AND ARCHITECTURES

(75) Inventor: James W. Holm-Kennedy, Honolulu, HI (US)

(73) Assignee: University of Hawaii, Honolulu, HI (US)

( * ) Notice: Subject to any disclaimer, the term of this patent is extended or adjusted under 35 U.S.C. 154(b) by 196 days.

(21) Appl. No.: 12/807,188

(22) Filed: Aug. 30, 2010

Related U.S. Application Data

(63) Continuation-in-part of application No. 11/083,109, filed on Mar. 18, 2005, now abandoned.

(60) Provisional application No. 60/554,610, filed on Mar. 18, 2004, provisional application No. 60/554,612, filed on Mar. 18, 2004, provisional application No. 60/554,616, filed on Mar. 18, 2004.

(51) Int. Cl.
*H01L 21/331* (2006.01)
*H01L 21/70* (2006.01)

(52) U.S. Cl.
USPC .......................................... 438/314; 257/552

(58) Field of Classification Search .................. 257/290, 257/350, 552; 438/313–316
See application file for complete search history.

(56) References Cited

U.S. PATENT DOCUMENTS

| 4,804,633 | A | * | 2/1989 | Macelwee et al. | ............. 438/16 |
| 4,839,707 | A | * | 6/1989 | Shields | ........................ 257/350 |
| 4,885,623 | A | * | 12/1989 | Holm-Kennedy et al. | ... 257/290 |
| 5,095,351 | A | * | 3/1992 | Gotou | ........................ 257/552 |

* cited by examiner

*Primary Examiner* — Calvin Lee
(74) *Attorney, Agent, or Firm* — James Creighton Wray

(57) ABSTRACT

A new class of electronic devices suitable for Si IC incorporation and of diverse utility are described. The devices are useful for many sensing applications as well as for special circuit applications. Sensing applications include chemical and biochemical sensing, photo detection (UV, visible, IR and FIR), magnetic field sensing, electric field sensing, and force sensing. The devices are MEMs compatible. Sensor sensitivity is voltage and current tunable over a wide range. The devices further constitute a new and useful class of IC reference voltage devices. Selective non linear features are also achievable in support of non-linear device applications. These unique devices may be considered as distributed merged bipolar and FET structures. The new distributed channel bipolar devices (DCBDs) have a channel of a selected shape formed in a surface of a substrate by doping or by influencing of a coating. In the device structure, the channel acts as an NPN or PNO BJT collector or emitter.

32 Claims, 4 Drawing Sheets

DISTRIBUTED CHANNEL BIPOLAR DEVICES AND ARCHITECTURES

This is a continuation-in-part of application Ser. No. 11/083,109, filed Mar. 18, 2005 now abandoned, which claims the benefit of U.S. Provisional Application No. 60/554,610, filed Mar. 18, 2004, U.S. Provisional Application No. 60/554,612, filed Mar. 18, 2004, and U.S. Provisional Application No. 60/554,616, filed Mar. 18, 2004, which are hereby incorporated by reference in their entirety.

Applicant's own U.S. Pat. Nos. 4,885,623 and 5,466,348 are also incorporated herein by reference in their entireties.

BACKGROUND OF THE INVENTION

Biosensors have been and are being developed to detect, identify and quantify various biochemicals, ranging from proteins to toxins to RNA to c-DNA to oligos and to disease agents such as viruses, bacteria, spores and Prions. This list is by way of example, and is not intended to be complete. Some biosensors sense charge on the molecule. Many biochemicals carry a net charge. Electrophoresis methods and various blots exploit molecule net charge to affect physical separation of such molecules.

There is a significant problem with existing techniques such as electrophoresis and the various blots. These sensors are not specific in identifying the molecules in question unless significant post processing and labeling is employed. Further, a very large quantity of the tested biochemical is required for electrophoresis detection methodologies.

In many instances the number of molecules available for detection is very small and may be below the sensitivity threshold of the sensor, or may be problematic with respect to sensitivity. For example, some plasma proteins are of very low concentration. Toxins such as Botulinum toxin are notoriously hard to detect at lethal thresholds because of their very low lethal and sub-lethal, but still dangerous, concentrations. Mass spectroscopy requires a large number of molecules in order to achieve adequate detection sensitivity.

In the case of c-DNA and RNA sensing, the number of base molecules present may be low for adequate detection and determination of which one is trying to specifically identify. This is possible if, for example, only a few bacteria are present or the RNA is of low concentration. Virus RNA may be of low density. Only a small portion of the RNA molecule may provide the definitive identification signature. Overall this can lead to a relatively small amount of RNA actually involved in the definitive detection process, if only few bacterial or viruses are present.

In the case of proteins, the target molecule concentration may be very low in the sample. For example, with Prions (mad cow disease), if a fluid sample is taken from an animal's blood, the target protein concentration may be very low. With a rapid infection of humans, animals or plants with disease, the initial signature indicators may be present in only very small concentrations. For the very early stages of cancer, when one wishes to identify disease presence, definitive indicators may be present in only very small concentrations. An example includes the four or so proteins reported as indicative of ovarian cancer. Where only small concentrations of target molecules are available, mass action effects can result in the bound target concentration being very low. A small percentage of the actual receptors or recognition units, specific antibodies, available for bonding results in a very small detection signal, for example, as is the case of a lethal concentration of botulinum toxin. At the very earliest onset of disease, the density of indicative proteins, viruses, antibodies and bacteria may be very low, requiring putting a very high sensitivity burden on the sensing approach.

Sensors for the detection of target molecules using charge and/or chemical potential have been reported. One of Applicant's most recent biosensor patents discusses sensing chemical potential, i.e., voltage. The most commonly used charge sensing to date are those using electrophoreses methods, such as the various blots. Semiconductor charge sensors have long been highly prized due to their compatibility with integrated circuits and attendant low cost manufacturing processes. An example is the ImmunoFET that uses a conventional MOSFET, absent a metal gate, and employing a reference electrode in solution.

Some sensors sense a change in charge or chemical potential as a result of a chemical attachment to the gate region of the devices. Needs exist for sensitive sensors that can sense very low concentrations.

Contamination and pollution in water, air and foodstuff is a continuing threat to public health. Water contaminated with Pb, Hg, Dioxin, or other hazardous chemical substances is problematic. Air may be contaminated with hazardous chemicals, of which OSHA has a long list, either in the general environment, the home, the industrial workplace or the chemical factory. Food contamination is likewise problematic for public heath. The chemicals in question may be inorganic (such as Pb and Hg), organic (such as organic solvents) or biochemical such as viruses, bacteria, toxins and hazardous proteins.

Additional environmental threats arise from potential chemical use by terrorists. Such threats include the well-known toxins such as botulinum toxin and ricin, as well as many others. Another threat is that of explosives intentionally (such as bombs introduced by terrorists) or unintentionally (such as antipersonnel mines) found in some location.

There is a need for an electronic sensor that can detect such public health risk chemicals in water, air and foodstuffs. In general, such requirements include biosensors that may incorporate such specific chemical binding means as oligos, proteins and antibodies, for example.

SUMMARY OF THE INVENTION

The invention includes multiple applications CMOS compatible sensors, distributed channel bipolar devices (DCBDs), biosensors, force sensors, magnetic sensors and optical sensors. By making the active area of the sensor small and the depth of the doping and doping concentration small, the total number of charges in the channel is small. The devices include multiple terminal devices.

The invention has increased sensitivity for many uses, including chemical, magnetic field, electric field, force, optical and far infrared sensing. In basic semiconductor charge sensors, sensitivity is addressed by channel doping, geometrical considerations, active area, MOS structures, buried channel structures, channel thickness, channel dimensions, biases affecting channel charge, and biases affecting channel operating condition.

By making the active area of the sensor small and the depth of the doping and doping concentration small, the total number of charges in the channel is small. Thus, when charged molecules are attached to the active gate area and the molecular net charge's electric field terminates on the underlying channel, the number of free conducting charge carriers in the channel is modulated by precisely the number of charges on the gate. Thus, the fewer the charges in the channel, the larger the percentage change of the charge numbers in the channel and the larger the percentage change of the channel resistance under various operating conditions.

The devices include four terminal devices. Additional terminals may be added including multiple channels, multiple emitters, multiple bases and multiple gates. All of these have utility. The sensor has many chemical sensing applications. By way of example, such applications include, but are not limited to, those listed in Chart I.

Of particular interest is the sensing of biochemical molecules. By way of example, such molecules include, but are not limited to, those shown in Chart II.

The DCBD is used for, but not limited to, chemical, magnetic field, electric field, charge, chemical potential, nuclear, electromagnetic waves such as microwaves or RF signals, temperature, voltage, current, force, optical and far infrared sensing.

DCBDs of this invention may incorporate multiple gates, multiple emitters and/or multiple collectors.

The target molecules may include biomolecules from plants, animals and humans.

This invention has significant use in many sensor areas ranging from biomedical sensors to photodetectors to magnetic sensing to force sensing, and so on. The device sensitivity is voltage and current tunable. This device has significant complexity, and it unlikely that anyone else would have thought of it. For perspective, in prior years we made the vertical architecture devices and analyzed them as well. The inventor has experience and confidence in the basic features of both the charge transport features and applications. Magnetic sensing was tested previously for the vertical devices and showed good sensitivity with the possibility of increasing that sensitivity even further, as well as demonstrating sensitivity tunability. The lateral devices which are addressed by this application have sufficiently significant novelty to acquire coverage in a patent.

Other applications include designed non-linear behavior which is very useful for mixing, harmonic generation, and is an important new semiconductor device.

The invention is complicated from a charge transport point of view.

The DCBD has much higher sensitivity for many applications than more conventional semiconductor sensors. The sensors can operate from gate linked sensing (biosensing), base current sensing (e.g., sensitive photodetector), nuclear particle sensing, pyroelectric sensing, etc.

It is highly unlikely that any one has come up with the actual lateral DCBD, although some structures may look similar. Further, how the device is operated is central to getting the desired DCBD behavior.

The huge advantages of this device include very strong non linearities which can be biased so that extremely small changes in biasing parameters such as base current (e.g., photo current or photodetection) and gate bias (charges or voltage) provide sensitive detection. There are many operating modes with advantageous sensing means.

These and further and other objects and features of the invention are apparent in the disclosure, which includes the above and ongoing written specification, with the claims and the drawings.

DETAILED DESCRIPTION OF THE PREFERRED EMBODIMENTS

Figure 1:
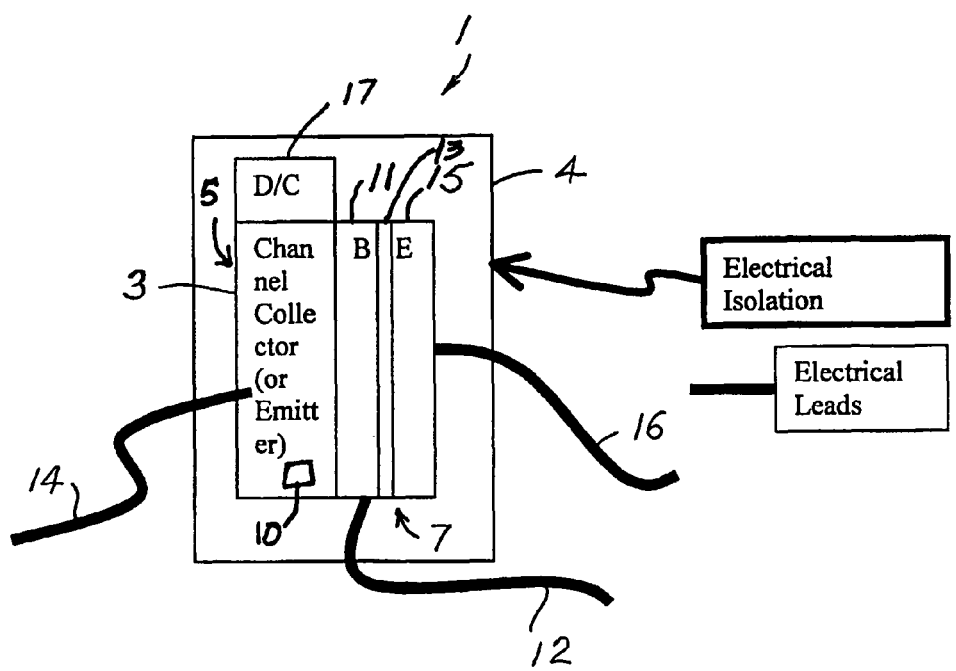
FIG. 1 shows a lateral DCBD with a MOSFET channel.

Basic Structures for the inventions include lateral distributed channel bipolar devices 1 (DCBDs), as shown in FIG. 1, which has a merged MOSFET and BJT, with the BJT being a lateral BJT. FIG. 1 shows a lateral DCBD 1 with a MOSFET channel 3 formed in substrate 4. In this example, the channel 3 is an n channel MOSFET 5 with an NPN integrated BJT 7. The n-channel MOSFET acts as a distributed channel emitter or distributed collector. The channel 3 functions as a distributed collector (or as distributed emitter), and the channel is controlled by a top gate bias and a back gate bias. The base 11 of the transistor is the substrate for the MOSFET. Transistor 7 has emitter E 15, base B 11 and PN junction depletion region 13 between the base and the emitter. The devices may be an n channel with an NPN transistor or a p channel with a PNP transistor. In one embodiment, chemicals 10 on a surface of the channel 3 influence current in the base 11, emitter 15, and channel 3.

In FIG. 1, the BJT emitter 15 is an N+ (NPN) region laterally separated from the collecting channel by a base width. The MOSFET channel 3 can be the BJT collector or the BJT emitter. The MOSFET gate may be selectively shaped to provide a desired electrical function. The base 11 width may be inhomogeneous, with a varying width along the channel collector 3. The channel collector may be shaped to provide a pre-selected attractive function and to enhance certain useful electrical characteristics. Graded doping may be used. Mesa etching and other means may provide selective isolation of key portions of the device. Multiple emitters may be used. Multiple collectors may be used. Combination of p and n channel devices may be used to provide a complimentary or other device combination. Various characteristics are achieved by controlling the drain voltage, base current, collector to base voltage and gate bias. It is noted that the transconductance threshold may be shifted by the back gate bias using the body effect. Electrical leads 12, 14, 16 are connected to the base 11, channel 3 and emitter 15, respectively. A drain/collector DC 17 is connected to the channel 3. A narrow regional 13 between the base 11 and the emitter 15 is a depletion region. It is noted that gate bias may be from a conventional conducting gate or induced by attached charge, e.g., to an insulating gate, or arising from a contract potential with an incorporated medium.

Lateral buried channel DCBDs, as shown in FIGS. 1 and 2A-C include a merged buried channel FET and BJT, with the BJT being a lateral BJT. There are two gates present. The first is a top gate that is a PN junction or a metal semiconductor junction. The channel functions as a distributed collector and the channel conductance is controlled by a top gate bias and a back gate bias. The base of the transistor is the substrate for the FET, which may be thought of as a JFET. The combination of the BJT and distributed collector JFET comprise a new device with novel electrical characteristics. The new devices are not JFET, MESFET, MOSFET or BJT. The devices may comprise a buried n channel FET with an NPN transistor or a buried p channel FET with a PNP transistor.

Figure 2A:
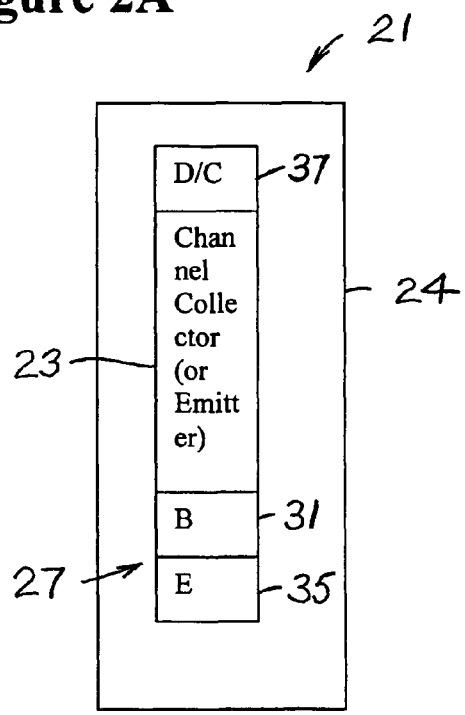
FIG. 2A is a top view of a lateral DCBD with a channel.

FIG. 2A is a top view of a lateral DCBD 21 with a channel 23 in a substrate 24. The channel is formed with an FET 27. The FET may be a MOSFET, JFET, MESFET or other FET structure. An emitter 35 is spaced from the channel 23 by a base 31. A drain/collector DC 37 is connected to the other end of channel 23.

Figure 2B:
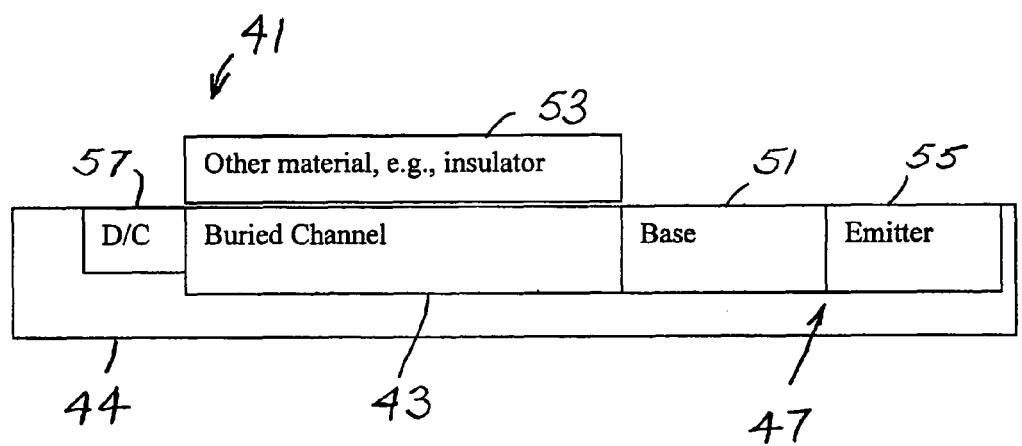
FIG. 2B is a cross section of a buried channel DCBD.

FIG. 2B is a cross section of a buried channel DCBD 41. Here, channel 43 the collecting channel or emitting channel in substrate 44 is a doped layer or heterostructure layer that self biases as a result of the collected or emitted current in the BJT. Base 51 is connected to the buried channel 43 and emitter 55 is connected to the base. The other material/insulator coating 53 on the buried channel 43 affects conductance of the channel. A back gate bias option enables additional FET channel conductance control and sensitivity control.

Figure 2C:
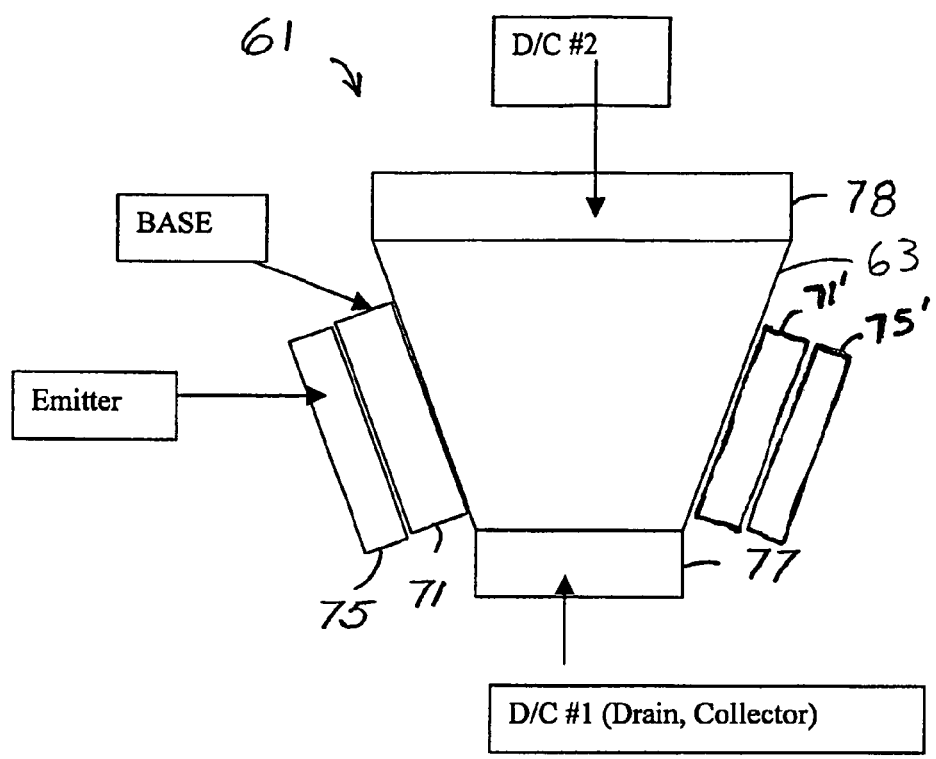
FIG. 2C shows a gate geometry example.

FIG. 2C shows a gate geometry and FET structure example in a DCBD 61. The channel collection regions 63, for both the MOS DCBD and the JFET DCBD and the MESFET DCBD, have a useful geometrical shape. Multiple emitters 75, 75' in the substrate are separated from the channel 63 by multiple bases 71, 71'. Channel 63 is differentially shaped between the multiple drain/collectors 77, 78. The multiple bases 71, 71' and the multiple emitters 75, 75' are mounted on lateral portions of the channel 63 between the multiple drain/collectors 77, 78. The drain/collector 77, 78 contacts #1 and #2 and emitters 75 and bases 71 provide multiple operational functionality.

The BJT emitter 75 is a N+ (NPN) region laterally separated from the collecting channel 43 by a base width 71. The JFET channel 43 shown in FIG. 2B can be the BJT collector or the BJT emitter. The JFET gate 63 FIG. 2E and channel 43 FIG. 2B may be selectively shaped to provide a desired electrical function. The base 71 width may be inhomogeneous, with a varying width along the channel collector 43. The channel collector 43 may be shaped to provide a pre-selected attractive function and to enhance certain useful electrical characteristics. Graded doping may be used. Mesa etching and other means may provide selective isolation of key portions of the device. Various characteristics are achieved by controlling the drain voltage, base current and collector to base voltage. The transconductance threshold may be shifted by the back gate bias using the body effect. The JFET structure is used by way of example. It will be obvious to those of skill in the art on reading this specification that the FET may also be an FET structure different from a JFET. For example, the FET structure could be MOSFET, a MESFET or other FET structure. The channel in such latter cases takes on the usual FET form (i.e., a gate induced inversion channel for an inversion type MOSFET).

Figure 3:
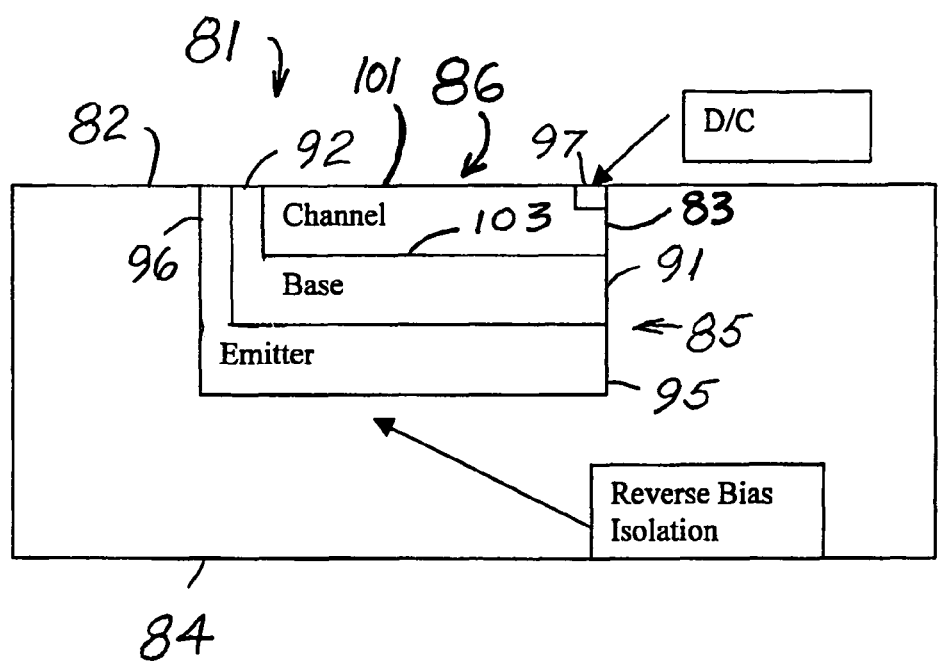
FIG. 3 shows a basic configuration of a vertical DCBD.

Vertical buried channel DCBDs 81, as shown in FIG. 3, include a merged buried channel FET 86 and BJT 85, with the BJT 85 being a vertical BJT with the collector or emitter 95 placed vertically with respect to the collecting channel 83 within substrate 84. FIG. 3 shows a basic configuration of a vertical DCBD 81. The collecting channel 83 may be located at the surface 82 above the BJT 85 structure or buried beneath the BJT structure. There are two gates present: a top gate 101 and a bottom gate 103. The first is the top gate 101 that is a PN junction. The invention can have an MOS gate controlling part of the buried channel conduction through depletion or accumulation and it is still a top gate on a different structure than the original issue patent's vertical DCBD structure or a metal semiconductor junction. Electrical connections 92, 96 are respectively connected to the buried base 91 and the buried emitter 95.

The channel 83 functions as a distributed collector or distributed emitter, and the channel conductance is controlled by a top gate bias and a back gate bias. The base 91 of the transistor 85 is located between the channel 83 FET and the BJT emitter 95. The combination of the BJT and distributed collector JFET comprises a new device with novel electrical characteristics. Said new devices are not a JFET, MESFET or BJT. The devices may comprise a buried n channel with an NPN transistor or a buried p channel with a PNP transistor. Drain/collector 97 is connected to channel 83.

The BJT emitter 95 in this example is a N+ (NPN) region vertically separated from the collecting channel 83 by a base width 91. The JFET or MESFET channel can be the BJT collector or the BJT emitter. The JFET gate and channel may be selectively shaped to provide a desired electrical function. The channel collector may be shaped to provide a pre-selected attractive function and to enhance certain useful electrical characteristics. Graded doping may be used. Mesa etching and other means may provide selective isolation of key portions of the device. Various characteristics are achieved by controlling the drain voltage, base current and collector to base voltage. The transconductance threshold may be shifted by the back gate bias using the body effect. The invention can also use a PNP structure.

Combined vertical and horizontal DCBDs include combinations of the devices described above, and also may include buried or convention FET channels. Not shown in figures are potential combinations of all embodiments.

Similar structures may integrate other DCBD structures such as MESFETs, HEMTs, and various hetero-structure devices.

It is noted that the buried channels may have conductivity inhomogeneities in all directions, said inhomogeneities being selected to provide a desirable electrical function. For example, a buried channel may be doped to have a higher conductivity at one end of the channel than at the other end of the channel.

While not adequate to describe the full usefulness of the DCBDS described herein, the devices may be thought of, in a limited way, as BJTs with distributed channel emitters or distributed channel collectors. Alternatively, the devices may be thought of as FETs with distributed BJT sources or distributed BJT drains.

Because of the uniqueness of the structures, especially the buried channel structures, it is noted that the channel may be biased to selectively affect the attraction, repulsion, binding or dissociation of target biochemical species. Further, groupings of such chemicals may occur. Molecules responding to the electric field, created by a biased gate region projecting an electric field into the surrounding medium containing the target species, place an electrostatic force on the dipoles and charged molecules. The dipoles may be permanent dipoles or induced dipoles, and the charges may be positive or negative.

The applications in biosensors apply to many types of biochemicals cells, bacteria, viruses, proteins, toxins and a diversity of systems or targets.

While the invention has been described with reference to specific embodiments, modifications and variations of the invention may be constructed without departing from the scope of the invention, which is defined in the following claims.

CHART I

| Biosensors | Chemical Sensors | Magnetic Sensor |
|---|---|---|
| Force Sensors (accelerometers, microphones, flow sensors, etc.) | Microfluidic Sensors | Reference Voltage Devices |
| Transconductance Device | Gain Device | Switch |
| Threshold Sensor | PhotoDetector | PhotoEmitter |
| Nuclear Radiation Detector | Modulator | Oscillator |
| Spatial Photo Detector | Spatial Biosensor | |

CHART II

| Nucleic Acids | Oligos | Viruses | Acids |
|---|---|---|---|
| | c-DNA | Bacteria and it component parts such as epitopes, membranes, proteins, Etc. | Bases |
| | RNA | Cells (all kinds) | Chemicals affecting cell function and body function |
| | DNA | Membranes | Isolelectric Molecules (conditions) |
| | Other | Receptors | pH and pH influenced molecules |
| Antibodies | | Proteins | Ions |
| Enzymes | | Hormones | Toxins |
| BioDefense Agents | | Salts | Buffering Agents |
| Pain Receptors | | Insecticides | Chemical Agents |
| Explosives | | Water Quality Monitoring Chemicals | Pb, Hg, and other hazardous metals |
| Other | | | |

We claim:

1. A method of semiconductor sensing comprising providing a distributed channel bipolar device (DCBD), providing a substrate and providing a distributed collector-emitter channel in the substrate, providing a base in the substrate, connecting the base to the collector-emitter channel, and providing an emitter in the substrate, spacing the emitter from the channel by the base, providing a drain, connecting the drain to the channel in the base, and providing electrical leads connected to the channel, wherein the channel functions as a distributed collector and/or distributed emitter, and the channel is controlled by a top gate bias and/or a back gate bias.

2. The method of claim 1, wherein the base and the emitter for controlling current in the channel, base and emitter current according to influence on the channel by chemicals on a surface of the channel.

3. The method of claim 2, wherein the drain influences the current.

4. The method of claim 1, wherein the method is used for chemical sensing, force sensing, optical sensing, photodetection, magnetic sensing, temperature sensing, electromagnetic sensing, chemical sensing, electric field sensing, voltage sensing or sensing IC functional device electrical characteristics.

5. The method of claim 1, wherein the DCBD has multiple gates, multiple emitters and/or multiple collectors.

6. The method of claim 1, wherein the DCBD is used for chemical, magnetic field, electric field, force, optical and far infrared sensing.

7. A semiconductor apparatus comprising a distributed channel bipolar device (DCBD) having a substrate and a distributed collector emitter channel in the substrate, a base in the substrate, a base in the substrate connected to the collector emitter channel, and an emitter in the substrate spaced from the channel by the base, a drain/collector emitter connected to the channel and electrical leads connected to the channel, wherein the channel functions as a distributed collector and/or a distributed emitter, and the channel is controlled by a top gate bias and/or a back gate bias.

8. The apparatus of claim 7, wherein the base and the emitter for controlling current in the channel, base and emitter according to influence on the channel by chemicals on a surface of the channel by the gate.

9. The apparatus of claim 8, wherein the drain/collector bias influences the current.

10. The apparatus of claim 8, wherein the gate influence comprises chemicals on a surface of the channel.

11. The apparatus of claim 7, wherein the channel is an n channel FET with an NPN integrated BJT, and the n-channel FET acts as a distributed channel or distributed collector.

12. The apparatus of claim 11, wherein the base of the transistor is the substrate for the FET.

13. The apparatus of claim 11, wherein the BJT emitter is an N+ (NPN) region laterally separated from the collecting channel by a base width, and the FET channel is the BJT collector or the BJT emitter.

14. The apparatus of claim 11, wherein the FET channel is selectively shaped.

15. The apparatus of claim 11, wherein the channel is constructed with graded doping in the substrate.

16. The apparatus of claim 11, wherein the channel is constructed with mesa etching in the substrate for providing selectively isolated portions of the channel.

17. The apparatus of claim 11, further comprising multiple emitters in the substrate separated from the channel by bases.

18. The apparatus of claim 11, further comprising multiple drain/collectors connected to the channel.

19. The apparatus of claim 18, wherein the channel is differentially shaped between the multiple drain/collectors, and the base and emitter are mounted on a portion of the channel between the multiple drain/collectors.

20. The apparatus of claim 11, wherein the base has an inhomogeneous feature varying along the channel collector.

21. The apparatus of claim 7, wherein the DCBD has multiple gates, multiple emitters and multiple collectors.

22. The apparatus of claim 7, wherein the DCBD sensor is used for chemical, magnetic field, electric field, force, optical and far infrared sensing.

23. The apparatus of claim 7, wherein the FET includes at least one FET selected from a group consisting of a MOSFET, a buried channel MOSFET, a buried channel FET, a JFET, a heterojunction FET, a MESFET, and an ISFET.

24. The apparatus of claim 7, wherein the channel is a p-channel FET with a PNP integrated BJT, and the p-channel FET acts as a distributed channel or distributed collector.

25. The apparatus of claim 24, wherein the base of the transistor is the substrate for the FET.

26. The apparatus of claim 24, wherein the BJT emitter is an P+ (PNP) region laterally separated from the collecting channel by a base width, and the FET channel is the BJT collector or the BJT emitter.

27. The apparatus of claim 24, wherein the FET channel is selectively shaped.

28. The apparatus of claim 24, wherein the channel is constructed with graded doping in the substrate.

29. The apparatus of claim 24, wherein the channel is constructed with mesa etching in the substrate for providing selectively isolated portions of the channel.

30. The apparatus of claim 24, further comprising multiple emitters in the substrate separated from the channel by bases.

31. The apparatus of claim 24, further comprising multiple drain/collectors connected to the channel.

32. The apparatus of claim 31, wherein the channel is differentially shaped between the multiple drain/collectors, and the base and emitter are mounted on a portion of the channel between the multiple drain/collectors.

* * * * *